(12) United States Patent
Harrison et al.

(10) Patent No.: US 9,592,661 B2
(45) Date of Patent: Mar. 14, 2017

(54) SYSTEM FOR DEPOSITING AN IMPRINT ONTO A SUBSTRATE

(71) Applicant: Church & Dwight Co., Inc., Princeton, NJ (US)

(72) Inventors: Michael J. Harrison, Princeton, NJ (US); Andrew Y. Oleson, Lambertville, NJ (US); William D. Platt, Lumberton, NJ (US); Richard Grotyohann, Hillsborough, NJ (US); Richard Wilheim Janse van Rensburg, Cambridge (GB)

(73) Assignee: Church & Dwight Co., Inc., Princeton, NJ (US)

( * ) Notice: Subject to any disclaimer, the term of this patent is extended or adjusted under 35 U.S.C. 154(b) by 0 days.

(21) Appl. No.: 14/774,278

(22) PCT Filed: Mar. 13, 2014

(86) PCT No.: PCT/US2014/026426
§ 371 (c)(1),
(2) Date: Sep. 10, 2015

(87) PCT Pub. No.: WO2014/151772
PCT Pub. Date: Sep. 25, 2014

(65) Prior Publication Data
US 2016/0031205 A1 Feb. 4, 2016

Related U.S. Application Data

(60) Provisional application No. 61/789,879, filed on Mar. 15, 2013.

(51) Int. Cl.
*B41F 3/00* (2006.01)
*B41F 3/20* (2006.01)
(Continued)

(52) U.S. Cl.
CPC .................. *B41F 3/20* (2013.01); *A61F 6/04* (2013.01); *B29C 59/021* (2013.01); *B29C 59/026* (2013.01); *A61F 2006/048* (2013.01)

(58) Field of Classification Search
CPC .... A61F 6/04; A61F 2013/15105; A61F 6/00; A61F 2006/048; B41F 3/20; B41M 1/40; C09D 11/10; B41J 3/4073
See application file for complete search history.

(56) References Cited

U.S. PATENT DOCUMENTS 2,244,592 A  6/1941 Youngs
3,239,365 A  3/1966 Petry
(Continued)

FOREIGN PATENT DOCUMENTS

EP  0316659 A2 *  5/1989  ............... A61F 6/04
EP  2540909 A2  1/2013
(Continued)

OTHER PUBLICATIONS

Non-Final Office Action for U.S. Appl. No. 14/774,595, mailed on Aug. 1, 2016, pp. 1-56, which corresponds to this present application.

*Primary Examiner* — Matthew G Marini
(74) *Attorney, Agent, or Firm* — Church & Dwight Co., Inc.

(57) ABSTRACT

A system for depositing an imprint onto a substrate includes a deposition surface having at least one outlet disposed therein, a substrate holder for holding the substrate against the deposition surface, means operatively associated with the deposition surface for supplying a material through said at least outlet to deposit said material onto the substrate, and a spacer member disposed in contact between the deposition surface and the substrate.

20 Claims, 9 Drawing Sheets

(51) Int. Cl.
    *A61F 6/04*     (2006.01)
    *B29C 59/02*     (2006.01)

(56) References Cited

U.S. PATENT DOCUMENTS

| | | |
|---|---|---|
| 3,411,982 A | 11/1968 | Kavalir et al. |
| 4,840,188 A * | 6/1989 | Heidenfelder ............ 128/844 |
| 5,447,752 A | 9/1995 | Cobb |
| 5,712,018 A | 1/1998 | Frisch |
| 5,827,577 A | 10/1998 | Spencer |
| 6,036,993 A | 3/2000 | Frazzitta |
| 6,096,412 A | 8/2000 | McFarland et al. |
| 6,182,661 B1 | 2/2001 | Solanki et al. |
| 6,308,708 B2 * | 10/2001 | Strauss et al. ............ 128/842 |
| 6,541,101 B1 | 4/2003 | Cook et al. |
| 6,732,735 B1 | 5/2004 | Snell |
| 8,104,097 B2 | 1/2012 | Hamann |
| 8,110,266 B2 | 2/2012 | Chen et al. |
| 2003/0234474 A1 * | 12/2003 | Williams .................... 264/553 |
| 2006/0115653 A1 | 6/2006 | Soerens et al. |
| 2007/0157559 A1 | 7/2007 | Till |
| 2007/0231525 A1 | 10/2007 | Bodwell et al. |
| 2008/0142021 A1 | 6/2008 | Van Hook |
| 2011/0209634 A1 | 9/2011 | Sabia et al. |
| 2012/0042795 A1 * | 2/2012 | Walker ...................... 101/123 |
| 2012/0073580 A1 | 3/2012 | Chuah et al. |
| 2012/0181726 A1 | 7/2012 | Platt et al. |
| 2013/0017373 A1 | 1/2013 | Wu et al. |
| 2013/0187963 A1 | 7/2013 | Kohrs et al. |
| 2014/0007883 A1 | 1/2014 | Nguyen et al. |
| 2014/0109917 A1 | 4/2014 | Nguyen et al. |

FOREIGN PATENT DOCUMENTS

| | | |
|---|---|---|
| WO | 01/00748 A1 | 1/2001 |
| WO | 2006/081817 A1 | 8/2006 |

* cited by examiner

SYSTEM FOR DEPOSITING AN IMPRINT ONTO A SUBSTRATE

CROSS-REFERENCE TO RELATED APPLICATION

This application is related to U.S. Provisional Patent Application Ser. No. 61/789,879 filed Mar. 15, 2013 and takes priority therefrom.

FIELD OF THE INVENTION

The present invention relates to deposition processes, and more particularly, systems for depositing an imprint onto a substrate.

BACKGROUND OF THE INVENTION

Printing is a process of depositing a substance onto the surface of a substance receiving substrate to produce graphic images (e.g., text and designs). A typical example of printing involves depositing ink on paper using a printing press. The development of print technologies has provided major progress in many areas on a large scale basis including the dissemination of information and the manufacture of goods relying on such technologies. Two print methods commonly used for depositing or printing graphic images onto the receiving substrate are lithographic printing and screen printing.

Lithographic printing utilizes printing plates having patterns formed from a series of grooves into which a thick ink is initially deposited with a suitable applicator. The grooves are configured for retaining a quantity of ink, while the areas adjacent to the grooves are rendered free of ink through careful wiping and scraping. The corresponding pattern is transferred after impressing the ink-loaded grooves onto the substrate surface with sufficient pressure whereby the surface contacts the ink retained in the grooves. This method of printing is relatively inexpensive and the resolution, density and quality of the printed image is generally adequate. However, when used on soft, elastomeric materials, the printed images are less satisfactory.

Screen printing is a print method suitable for use on a wide range of materials including textiles, ceramics, wood, paper, glass, metal and plastic. The method involves the use of a woven mesh or screen supported on a frame. An ink-blocking stencil is formed by blocking off parts of the screen in the negative image of the print. The open, unblocked parts representing the positive image of the print permit passage of the ink unto the substrate surface. The ink is pressed through the open areas of the screen to deposit a sharp-edged image onto the substrate surface below. A fill blade or squeegee is generally used to force ink into the mesh openings by moving it across the stencil screen to promote transfer through capillary action. Screen printing is more versatile than traditional printing techniques. The surface does not have to be printed under pressure and it does not have to be planar or flat. Screen printing also provides good color depth, enhanced definition and overall better quality images.

High-throughput commercial printing utilizes solvent-based inks to ensure rapid drying and good adhesion to the substrate surface. However, such inks suffer several drawbacks. Certain substrates, such as those composed of an elastomeric material, are not compatible with such solvent-based inks. These inks are formulated with solvents that usually penetrate the elastomeric material causing temporary physical changes such as swelling. Although the elastomeric material eventually returns to its original state as the solvent evaporates, its physical properties including barrier integrity may be adversely affected. In addition to the problem of incompatibility with elastomeric materials, solvent-based inks contain components that pose potentially harmful health effects on humans through contact with such inks printed on such elastomeric materials.

Accordingly, there is a need for a system for depositing an imprint onto a substrate, especially tubular or cylindrically-shaped substrates. There is also a need for a system for depositing an imprint onto a substrate with improved precision and accuracy.

SUMMARY OF THE INVENTION

The present invention relates generally to a system for depositing an imprint onto a substrate. The system of the present invention is configured for depositing an imprint onto a substrate to produce graphic images including visual and/or tactile textures thereon. In this manner, the present invention can be implemented to form decorative and/or functional elements on the surface of the substrate. The system of the present invention is configured particularly for fabrication of articles that are at least substantially safe for prolonged contact with human tissue including the skin and mucous membranes.

In one aspect of the present invention, there is provided a system for depositing an imprint onto a substrate, including:
- a deposition surface having at least one outlet disposed therein;
- a substrate holder for holding the substrate against the deposition surface;
- means operatively associated with the deposition surface for supplying a material through the at least one outlet to deposit the material onto the substrate; and
- a spacer member disposed between the deposition surface and the substrate.

BRIEF DESCRIPTION OF THE DRAWINGS

The following drawings are illustrative of embodiments of the present invention and are not intended to limit the invention as encompassed by the claims forming part of the application.

DETAILED DESCRIPTION OF THE INVENTION

Figure 1:
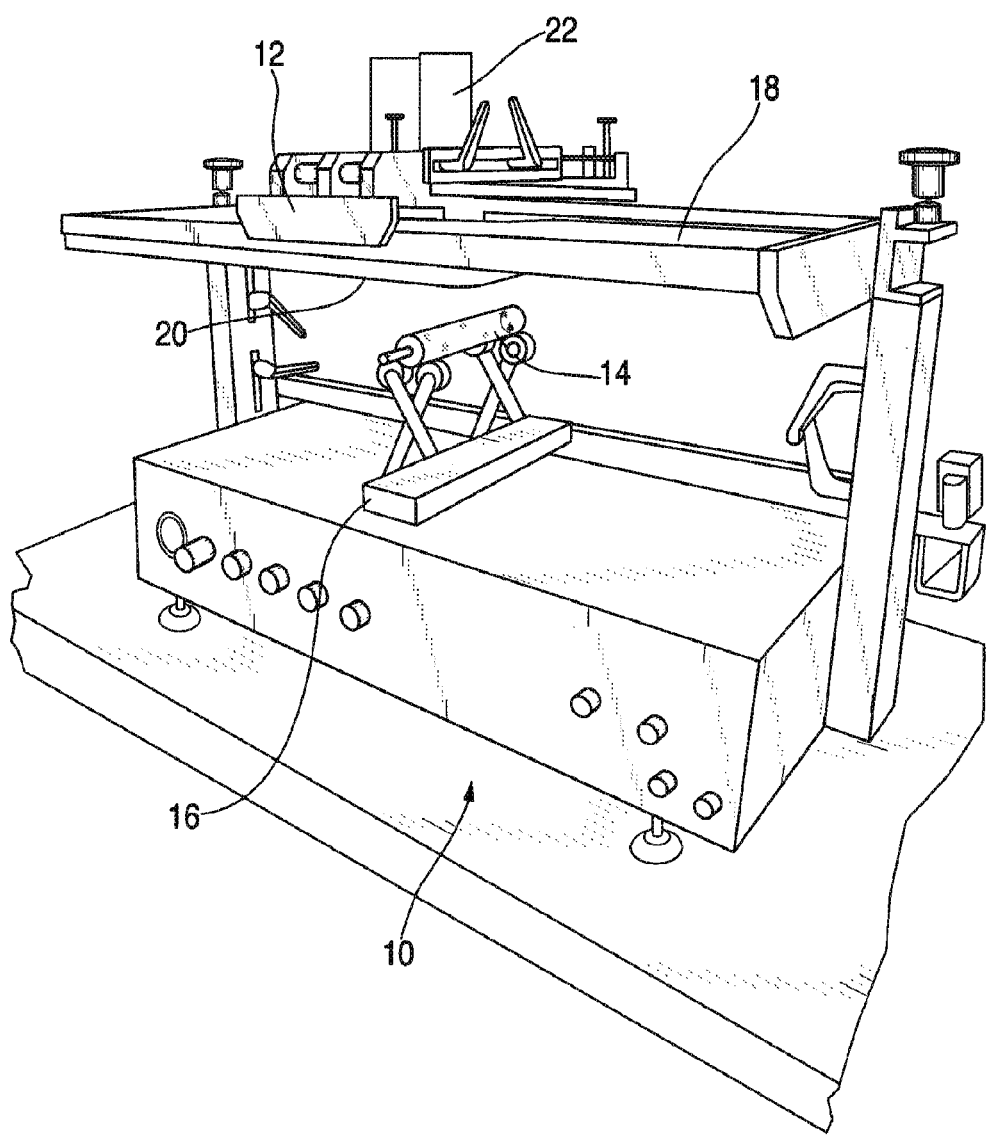
FIG. 1 is a perspective view of a system comprising a screen printer and a mandrel mounted carrier in one embodiment of the present invention.

The present invention is directed to a system for depositing an imprint onto a substrate. The system of the present invention is configured for depositing an imprint onto a substrate to produce graphic images including visual and/or tactile textures thereon. In this manner, the present invention can be implemented to form decorative and/or functional elements on the surface of the substrate. The system is particularly adapted for depositing an imprint on curvilinear substrates including tubular or cylindrically-shaped substrates. The system produces imprints on the substrate with improved precision and accuracy.

The system of the present invention can be optionally implemented for fabricating articles that are at least substantially safe for prolonged contact with human tissue including the skin and mucous membranes. The system of the present invention can be used in a range of products including, but not limited to, prophylactic devices such as condoms, prosthetics, medical devices and instruments, sports/athletic gear or equipment, footwear, dental products, eyewear, and the like.

The term "imprint" as used herein is intended to encompass any impression formed from the deposition material applied to or deposited on a surface of a substrate through suitable means including, but not limited to, printing processes, for producing graphic images including tactile and/or visual textures, and the like, on the corresponding substrate surface. The imprint may provide a decorative element, a functional element or combinations of both.

The term "textured imprint" as used herein is intended to refer to a particular form of imprint in which at least a portion of the impression is raised above the surface of the substrate. Such textured imprints are three-dimensional and provide depth to the substrate surface, and may include, but are not be limited to, rough textures, embossed textures, bumpy textures, ribbed textures, nubby textures, prickly textures, debossed textures, woven textures, and the like.

The system of the present invention utilizes a deposition material, preferably containing a water-based, highly elastic fluid material exhibiting robust adherence and viscosity suitable for deposition on the surface of the substrate. The preferred water-based, highly elastic fluid material is formulated to set or cure into a final solid form adhered to the substrate surface. The deposition material is especially compatible for use with elastomeric substrates and does not adversely alter or change the physical properties of the underlying elastomeric material. The deposition material is desirably screen-printable and sufficiently elastic accommodating extensions of up to 500%, adheres well enough to remain attached at these extensions, can be deposited at substantial thicknesses (over 1 mm), and is safe for human use.

The present invention can be implemented to produce textured imprints having three dimensional structures to impart graphic images including visual and/or tactile textures on the surface of the substrate. Using the deposition material, textured imprints embodying three dimensional images, including designs and/or textures, can be deposited and firmly bonded to the substrate surface. This is generally accomplished by formulating the deposition material with a sufficient degree of viscosity whereby the deposited material can support its own weight for a sufficient time, preferably one to several minutes, to dry or cure into a final, solid state. This is generally achieved through formulating a polymeric liquid (e.g., latex and elastomeric materials) with thickeners, fillers, viscosity modifiers and the like, thus enabling the deposited material to substantially retain its desired form, shape and structure as it cures or dries. The deposition material may be characterized by relatively high viscosity to yield a deposition thickness of at least about 100 microns, more typically between about 100 and 350 microns. The deposition material may be in the form of a viscous liquid, gel, dry foam, paste, and the like.

Figure 2:
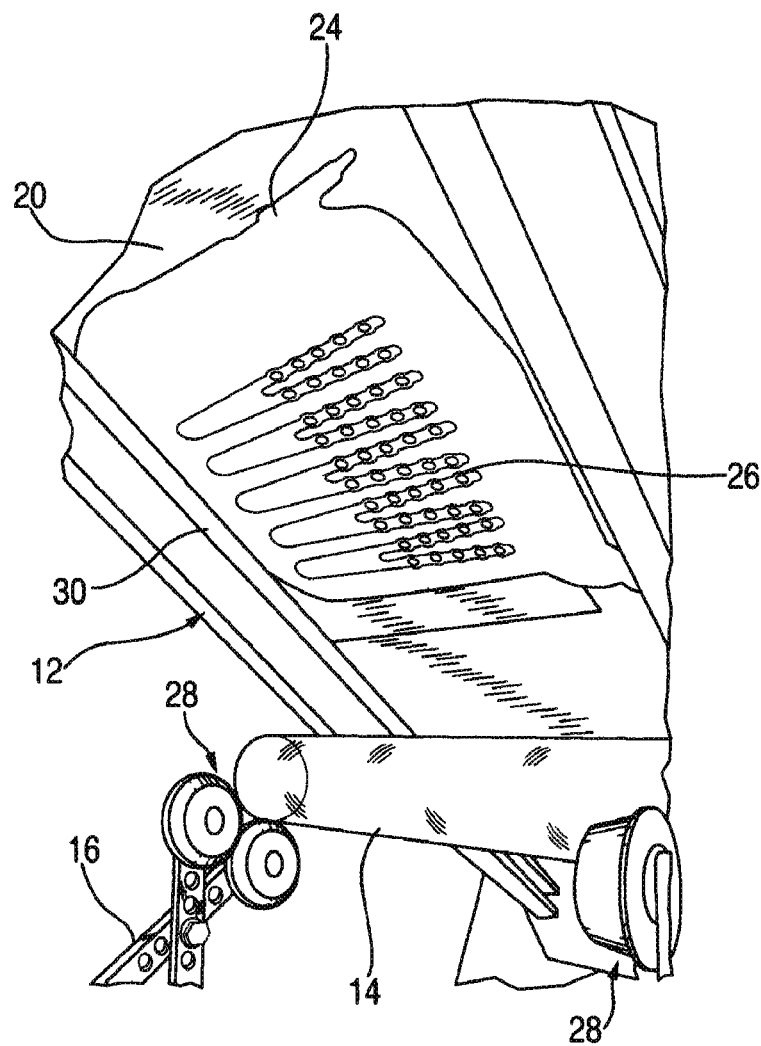
FIG. 2 is a perspective view from below of the system showing a deposition surface with two soft foam rubber 'tracks' (as indicated by the arrows) positioned under the screen on either side thereof in accordance with the present invention.

Referring to FIGS. 1 and 2, a system 10 adapted for depositing a deposition material onto a tubular substrate such as a condom to form an imprint, is shown for one embodiment of the present invention. The system 10 includes a compressed-air driven screen printer 12, a mandrel 14 on which the printer 12 may apply the deposition material thereon to form an imprint, and a carrier 16 for rotatively supporting the mandrel 14 thereon. The printer 12 is configured to movably slide back and forth on a set of racks 18, and includes a deposition surface 20 (as shown best in FIG. 2) and a deposition material supply assembly 22 having a squeegee or fill blade (not shown) operatively associated with the deposition surface 20 for supplying a deposition material to the deposition surface 20 as will be described hereinafter. The deposition surface 20 can be composed of, for example, a mesh or screen material.

As shown in FIG. 2, the deposition surface 20 includes a stencil 24 having a plurality of outlets 26 disposed therein collectively forming a negative image of the corresponding imprint to be made on the mandrel 14. The outlets 26 represent the points at which the deposited material will appear on the surface of the mandrel 14. It is noted that a tubular elastomeric material (e.g., polyurethane, latex, polyisoprene) can be used as a substrate by slipping it over the mandrel 14 during deposition. The mandrel 14 is supported on the carrier 16 via a wheeled assembly 28. This allows the mandrel 14 to rotate freely about its longitudinal axis.

The deposition surface 20 is placed in contact with the mandrel 14 with the longitudinal axis of the mandrel 14 oriented perpendicularly to the line of travel of the printer 12. As the printer 12 slides along the racks 18, the mandrel 14, being in contact with the deposition surface 20, is drawn rotationally across the stencil 24. The mandrel 14 rotates through frictional interaction with the deposition surface 20. The deposition material supply assembly 22 pushes the deposition material through the outlets 26 in the stencil 24. As the surface of the mandrel 14 contacts a corresponding portion of the stencil 24 and its outlets 26, the deposition material in the outlet 26 is pumped by capillary action to the mandrel 14 in a controlled and prescribed amount. As the mandrel 14 rolls away from the contacted portion of the stencil 24, the deposited material is left upon the surface producing an imprint thereon.

In a further embodiment of the present invention, the system 10 includes a spacer member 30 in the form of a pair of strips 30 composed of a resilient material affixed to the deposition surface 20 of the printer 12. The resilient material may be composed of soft foam rubber (e.g., polyisoprene), for example. The strips 30 form tracks disposed on either side of the stencil 24 for the mandrel 14 to travel as it is drawn rotationally across the deposition surface 20. The strips 30 may be affixed to the deposition surface 20 via any suitable means including, for example, double-sided adhesive tapes.

The strips 30 act as an effective means of adjusting the snap height between the surface of the mandrel 14 and the stencil 24. The strips 30 allow the user to adjust the imprint thicknesses up to about 350 microns. The strips 30 further ensure that the rotation of the mandrel 14 is at least substantially synchronized with its travel across the deposition surface 20. In the present embodiment of the invention, the strips 30 are about 1.5 mm thick, and multiple layers of strips 30 can be used for increasing thicknesses. The thickness of the strips 30 can be selected depending on the fill blade stiffness, mesh density and viscosity of the deposition material.

The deposition material used in the present system may be formulated for deposition or application onto substrates of elastomeric materials such as polyurethane, natural or synthetic latex, polyisoprene, and the like. The elastomeric substrate may be in the form of a film, coating, sheet, tubing, sheath, and the like. For example, the elastomeric substrate can be a condom. The deposition material is deposited as an imprint onto the surface of the condom, and set or cured to yield a final solid or dry form adhering firmly to the condom surface. The condom can readily be rolled up with the imprint into a packaged state. The resulting product is an imprinted condom that is non-toxic and safe for contact with human tissue including skin and mucosal membranes.

The deposition material includes a film-forming polymeric emulsion suspended in a suitable liquid medium. The liquid medium is preferably water. The polymeric emulsion may include natural polymers, synthetic polymers or a combination thereof. The film-forming polymeric emulsion may be in the form of a suspension of polymer microparticles.

In a preferred embodiment of the invention, the deposition material is formulated to set into a final solid or dry form upon deposition on the substrate, whereby the solid or dry form of the deposition material is specifically formulated to be non-toxic and safe for contact with human tissue including skin and mucosal membranes. The polymeric emulsion can be selected to harden by cross-linking of the polymers through the use of chemical additives (i.e., curing agents), ultraviolet radiation, electron beam or heat. Examples of ultraviolet curing polymers include, for example, DYMAX® 111-MSK, DYMAX® 1180-M-series, DYMAX® 1-20792 PDS, LOCTITE® 3381, and LOCTITE® 3321.

In a preferred embodiment of the present invention, the film-forming polymeric emulsion is composed of a polymer selected, for example, from latex polymers, acrylic polymers, polyisoprene polymers, polyurethane polymers, polyvinyl polymers, polyepoxide polymers, polyvinyl chloride polymers, styrenic block polymers and combinations thereof.

In a more preferred embodiment of the present invention, the film-forming polymeric emulsion includes a mixture of latex polymer and acrylic polymer. The amounts of latex polymer and acrylic polymer are from about 10% to 90% latex and from about 10% to 90% acrylic, preferably from about 40% to 60% latex and from about 40% to 90% acrylic, and more preferably about 55% latex and about 45% acrylic.

The deposition material includes a film-forming polymeric emulsion composed of polyurethane polymer. The deposition material offers a thermosetting material that does not dissolve in water or melt under heat once permanently cured, and can be used as an adhesive, or as a space-filler which is especially suitable for providing graphic images including tactile textures to a substrate surface. The preferred deposition material is also miscible with acrylic-based dyes or colorants, and remains highly elastomeric when cured. The deposition material can be deposited on a substrate surface with a thickness of at least about 100 microns, more typically between about 100 and 350 microns.

The deposition material comprises polyurethane polymer which is especially compatible with conventional printing techniques such as screen printing, and exhibits excellent stability and shelf-life at room temperature in the uncured state. Screens and other equipment could be cleaned of uncured polyurethane simply by scraping off the unwanted polyurethane polymer and wiping with an isopropanol tissue.

The deposition material may further include one or more excipients including, but not limited to, inks, colorants, pigments, thickeners, fillers, stabilizers, binders, and the like. The excipients may be selected to modify or alter physical and/or chemical properties of the deposition material including, for example, viscosity, adhesive strength, durability, deposition or print density, elasticity, flexibility, color, drying or curing requirements, and the like.

Examples of suitable colorants include acrylic-based inks (e.g., SPEEDBALL®), FLEXIVERSE® Violet 23, FLEXCOLORS® inks, BIRO® inks, and the like.

Examples of suitable fillers and thickeners include talc, CERAMOFIX™, HAKUENKA®, carbon fiber, cellulose fiber, KEVLAR® fiber, fumed silica in water (e.g., AERODISP® WR 8520), fumed silica powder (e.g., AEROSIL® 200, CAB-O-SIL®), rheology modifiers (e.g., ACRYSOL® RM8), polyurethane thickener (e.g., BORCHIGEL™ PW25), thickeners (e.g., EVONIK® TEGO® VISCOPLUS™ 3000, 3010, 3030, 3060), and the like.

Figure 3:
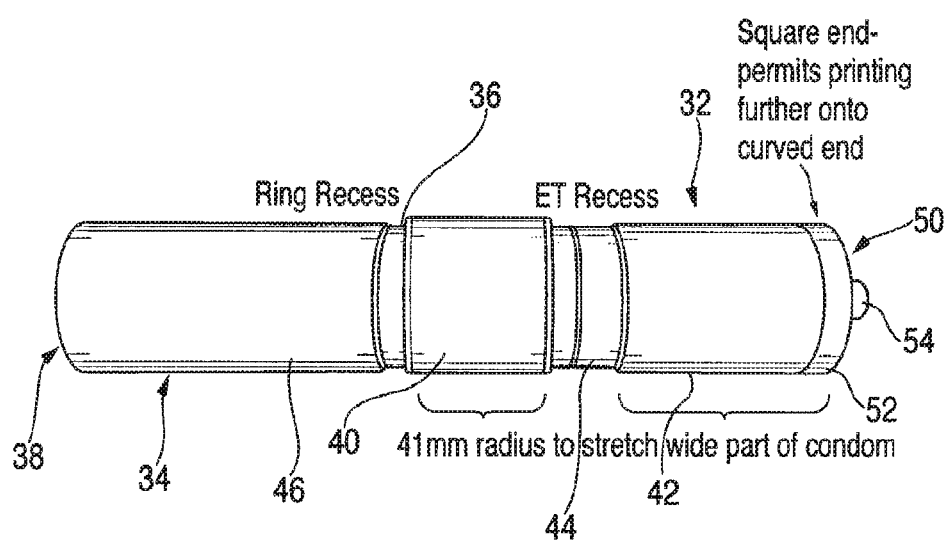
FIG. 3 is a side elevational view of a mandrel with recesses to accommodate other pre-print textured imprints and the roll-up ring of a condom for another embodiment of the present invention.

In reference to FIG. 3, a mandrel 32, configured for retaining thereon a tubular substrate thereon and composed of an elastomeric material, is shown for another embodiment of the present invention. The mandrel 32 is implemented in the system 10 shown in FIGS. 1 and 2 in the manner described above for depositing an imprint on the retained substrate. In a particular application, the mandrel 32 can be adapted to hold a condom for the deposition of imprints (e.g., graphic images including tactile textures) onto the condom surface, which may be smooth or textured (e.g., three dimensional surface features). The mandrel 32 includes cylindrical body 34 having a base end 38 and an opposed distal end 50. The body 34 includes a base portion 46, an intermediate portion 40, a distal end portion 42 proximate the distal end 50, a ring recess 36 disposed between the base portion 46 and the intermediate portion 40 and a texture recess 44 disposed between the distal end portion 42 and the intermediate portion 40. The mandrel 32 may further include a centrally-located protrusion or nipple 54 at the distal end 50 of the body 34.

A substrate in the form of tubular sheath such as a condom is placed on the mandrel 32 with the distal end 50 inserted therein. The ring recess 36 is configured for accommodating a rolled-up end or cuff portion (i.e., ring) of a condom to maintain a flat contact between the printer deposition surface 20 and the condom surface to be imprinted. The textured recess 44 is provided to accommodate portions of the condom having a textured surface. The position, length and depth of the textured recess 44 on the body 34 of the mandrel 32 may be modified depending on the configuration of the particular condom.

The intermediate portion 40 and distal end portion 42 are configured to stretch the portions of the condom to be imprinted radially outward. The distal end portion 42 further includes a squared edge portion 52 extending peripherally therearound. The distal end portion 42 radially expands the condom to produce a cylindrically flat surface compatible for depositing imprints thereon. In this manner, the edge portion 52 maximizes the area at the distal end of the condom printable by the printer 12.

Figure 4:
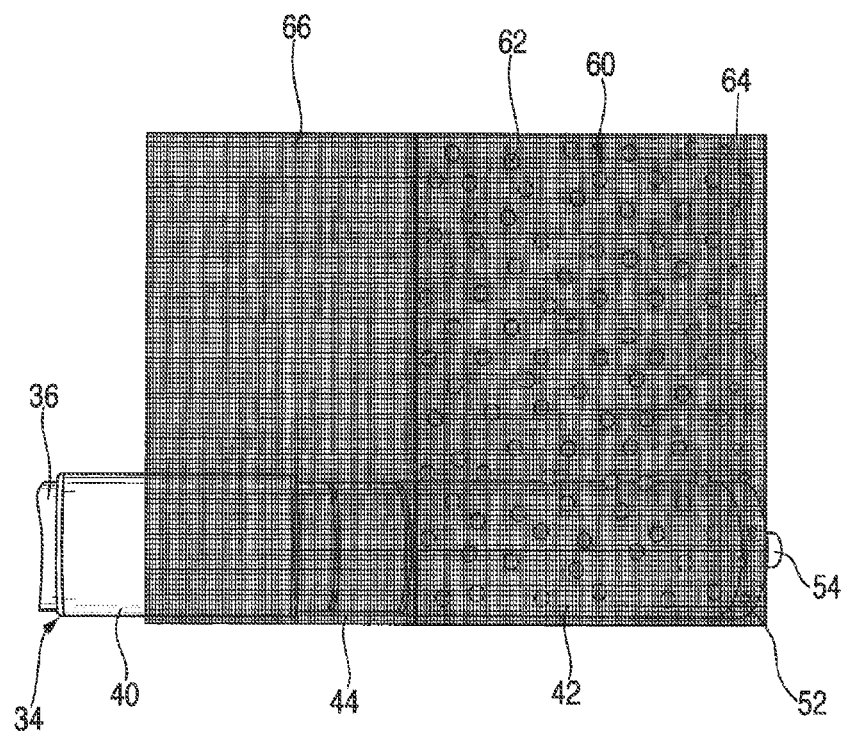
FIG. 4 is a partial side elevational view of the mandrel of FIG. 3 with a screen pattern superimposed thereon showing the manner in which an extension structure permits the smaller dots of the screen pattern to be printed around the shoulder in accordance with the present invention.

In reference to FIG. 4, a screen pattern 60 comprising an array of large dots 62 and small dots 64 for a stencil 66 in a screen printer (not shown) is superimposed over the mandrel 32 showing how the extension permits the small dots 64 to be printed around the shoulder portion of a condom (not shown). The dots 62 and 64 are more widely spaced on the stencil 66 because the resulting imprints contract back together when the condom is removed from the mandrel 32. With a condom mounted on the mandrel 32, it is noted that the area located at a shoulder portion of the condom is stretched over the distal end portion 42 of the mandrel 32. This provides a progressively stretched state when the surface of the condom is printed. Therefore, the pattern 60 in that area needs to be tailored so that it 'tapers' towards the nipple 54, so that when the condom relaxes, the pattern 60 contracts into the desired shape.

Figure 5A:
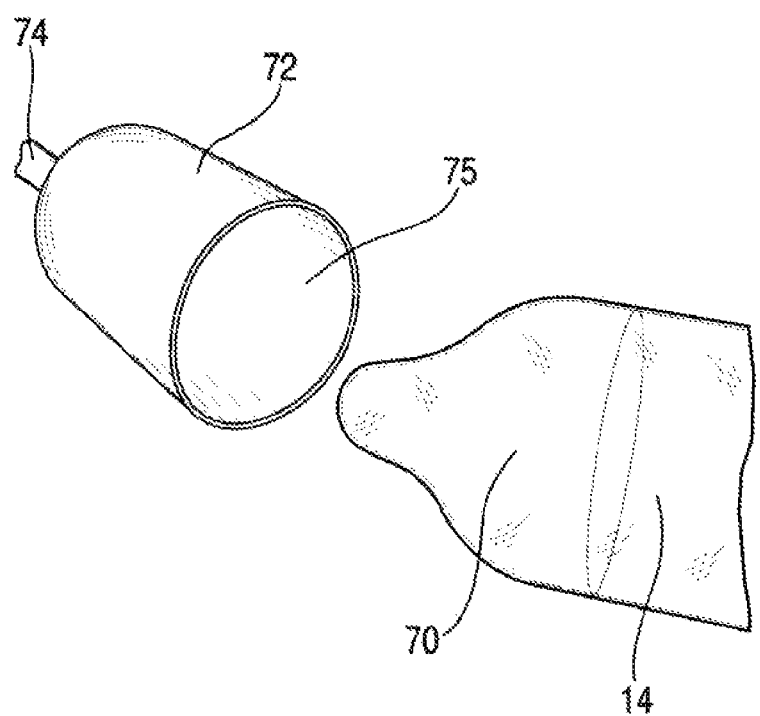
FIG. 5A is a partial assembly view of a mandrel with an extension cap configured for mounting on the distal end of the mandrel and maintained in position through vacuum means in accordance with one embodiment of the present invention.
Figure 5B:
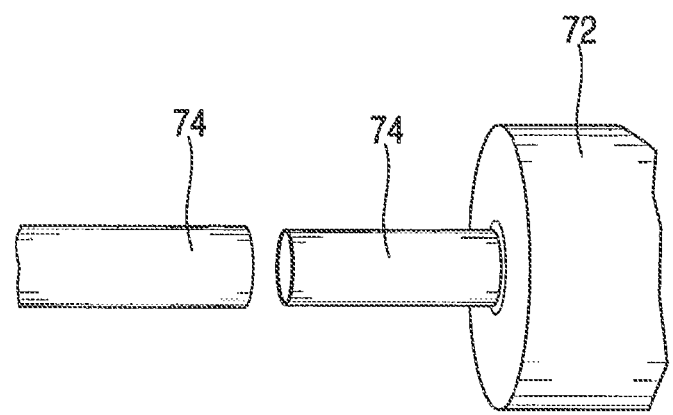
FIG. 5B is a partial assembly view of a coupling arrangement between a vacuum tube and the extension cap that permits free rotation therebetween in accordance with the present invention.
Figure 6:
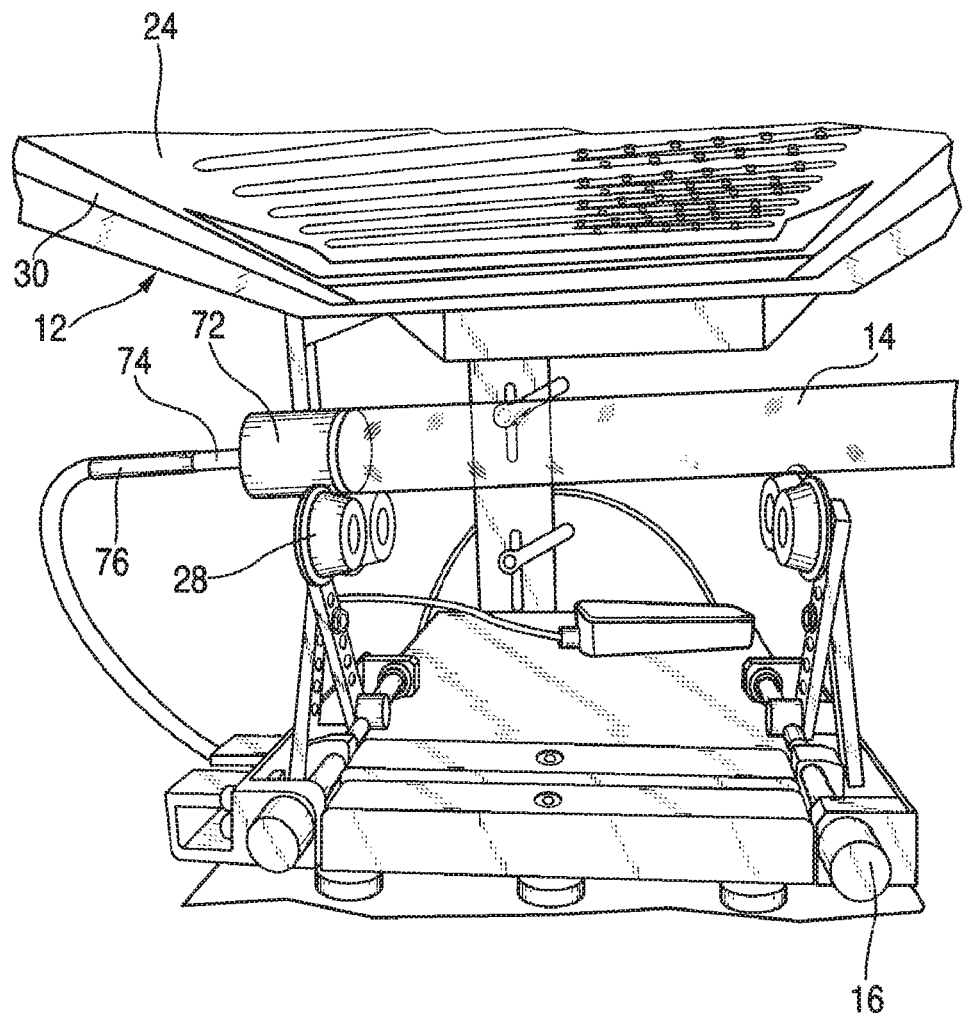
FIG. 6 is a partial perspective view of a mandrel supported on a carrier with the extension cap mounted thereon in accordance with the present invention.

Referring to FIGS. 5A, 5B and 6, there is shown a glass mandrel 14 configured for holding a tubular substrate such as, for example, a condom. The glass mandrel 14 includes a shoulder portion 70 extending therearound as shown best in FIG. 5A. The capacity of the screen printer 12 to print on areas about the shoulder portion 70 is limited by the configuration of the deposition surface 20 of the printer 12. As shown in FIG. 5A, an extension or end cap 72 may be used to "extend" the print area of the mandrel 14 and maximize the print width of the printer 12. The end cap 72 is in the form of a molded cup composed of a resilient material such as, for example, dental molding rubber, with a vacuum line 74 extending through a central portion thereof. The open end 75 of the end cap 72 is configured for a sealing fit about the distal end of the mandrel 14.

As shown in FIG. 5B, the vacuum line 74 of the end cap 72 is configured for insertion into a vacuum supply port 76 in a slip fit arrangement to provide a tubular swivel joint therebetween. The vacuum supply port 76 is attached to a vacuum generating source (not shown). The end cap 72 is securely retained on the distal end of the mandrel 14 through vacuum generated within the end cap 72 by the vacuum generating source. The tubular swivel joint formed between the vacuum line 74 and the vacuum supply port 76 allows the end cap 72 to rotate freely about its central longitudinal axis relative to the vacuum supply port 76 as the mandrel 14 rolls across the deposition surface 20 of the screen printer 12 during printing. In this manner, the end cap 72 is free to turn with the rotation of the mandrel 14.

As shown in FIG. 6, the end cap 72 is mounted on the distal end of the mandrel 14 and operatively engages the wheeled assembly 28 of the carrier 16. When the mandrel 14 contacts the stencil 24, the end cap 72 engages the spacer member 30 disposed on the deposition surface 20. As the mandrel 14 rotates across the stencil 24, the end cap 72 engages the corresponding spacer member 30 and the wheeled assembly 28 of the carrier 16. This arrangement allows the stencil 24 to be positioned closer to the shoulder portion of the mandrel 14, thereby maximizing the print area on the mandrel 14.

EXAMPLE

Figure 7:
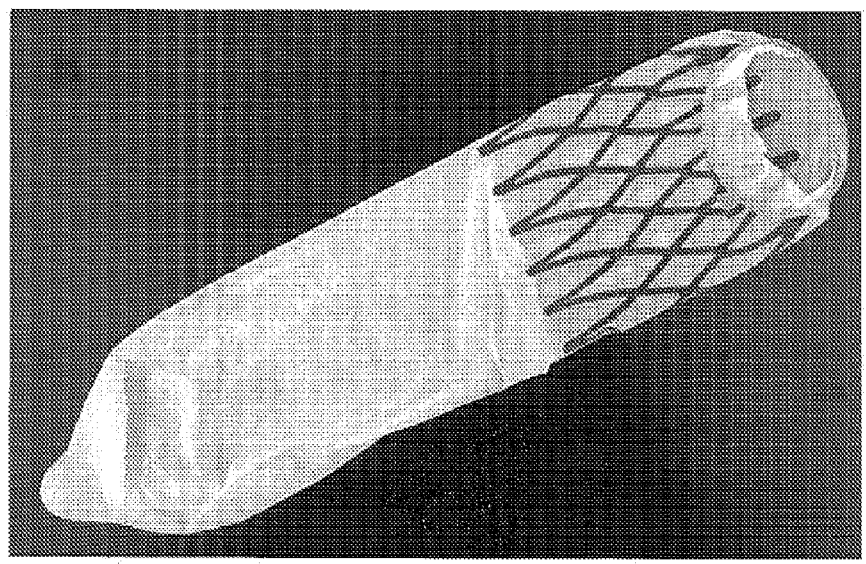
FIG. 7 is an elevational view of a condom with an imprint deposited thereon in accordance with the present invention.
Figure 8:
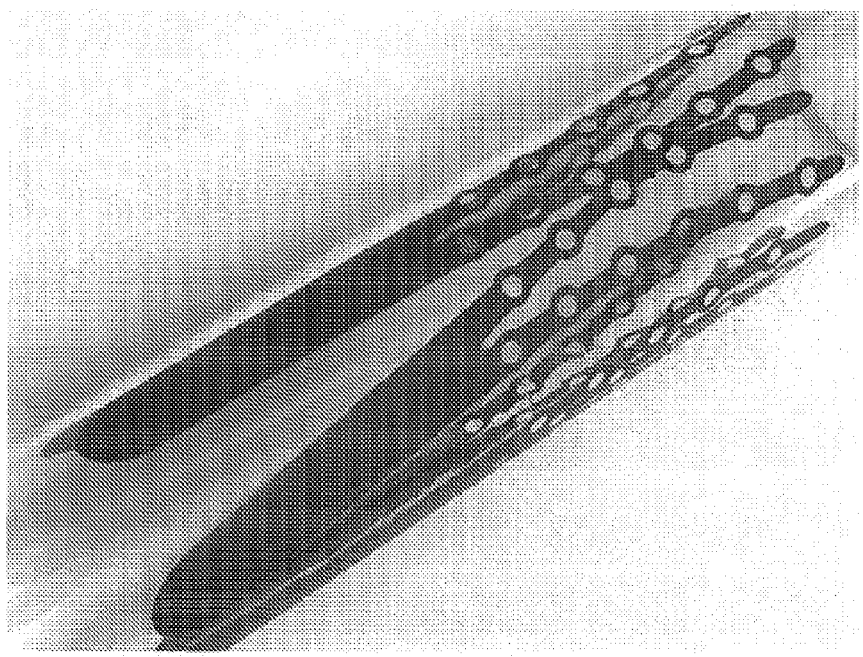
FIG. 8 is a perspective view of an imprint deposited on a glass mandrel in accordance with the present invention.

Referring to FIGS. 7 and 8, a test was implemented to print the image onto the glass mandrel and then transfer it during dipping. This test relied on the print easily releasing from the glass during dipping. The more easily the print is released the more precise the image. In particular, if the image moves during the critical period after the first dip while the latex is still fluid, there is a tendency for the image to be less precise. As shown in FIG. 7, the condom pictured shows a successful transfer. FIG. 8 shows a textured imprint formed from Revertex LA+Acrylic deposition material using a Screen Mesh 34 on a glass mandrel.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

What is claimed is:
1. A system for depositing an imprint onto a substrate, comprising:
   a deposition surface having at least one outlet disposed therein;
   a substrate holder for holding the substrate against the deposition surface, the substrate holder being rotatable and configured for movement across the deposition surface;
   means operatively associated with the deposition surface for supplying a material through said at least one outlet to deposit said material onto the substrate; and
   a spacer member formed of a resilient material disposed in contact between the deposition surface and the substrate, the spacer member forming a track for the movement of the rotatable substrate holder across the deposition surface.
2. The system of claim 1 wherein the substrate is composed of an elastomeric material.
3. The system of claim 1 wherein the substrate is tubular or cylindrical.
4. The system of claim 3 wherein the substrate is a condom.
5. The system of claim 1 wherein the spacer member comprises a pair of elongated strips affixed to the deposition surface, said strips each being located on opposing sides of said at least one outlet.
6. The system of claim 1 wherein the substrate holder is composed of a solid rigid material.
7. The system of claim 6 wherein the solid rigid material is glass.
8. The system of claim 1 wherein the substrate holder comprises a mandrel.
9. The system of claim 8 wherein the mandrel further comprises:
   a cylindrical body having a base end and an opposed distal end;
   said cylindrical body includes a base portion, an intermediate portion and a distal end portion; and
   a squared edge portion extending peripherally around said distal end portion.

10. The system of claim 9 further comprising a ring recess disposed radially around the mandrel body between the base portion and the intermediate portion thereof.

11. The system of claim 9 further comprising a texture recess disposed radially around the mandrel body between the intermediate portion and distal end portion thereof.

12. The system of claim 9 further comprising a protrusion located centrally at the distal end of the mandrel body.

13. The system of claim 9 further comprising a removable end cap operatively associated with a distal end portion of said mandrel.

14. The system of claim 13 wherein the removable end cap includes means for securing said end cap to the distal end of said mandrel.

15. The system of claim 14 wherein the securing means comprises a vacuum line extending through the center of said removable end cap.

16. The system of claim 1 wherein the deposited material comprises a film-forming polymeric emulsion suspended in a liquid medium.

17. The system of claim 16 wherein the film-forming polymeric emulsion comprises a polymer selected from the group consisting of latex polymers, acrylic polymers, polyisoprene polymers, polyurethane polymers, polyvinyl polymers, polyepoxide polymers, polyvinyl chloride polymers, styrenic block polymers and combinations thereof.

18. The system of claim 17 wherein the textured imprint comprises a deposition thickness of at least about 100 microns.

19. The system of claim 1 wherein imprint is textured.

20. The system of claim 1, wherein the substrate holder is tubular and has a longitudinal axis oriented perpendicular to the movement of the substrate holder across the deposition surface.

* * * * *